United States Patent
Van Valey

[11] Patent Number: 6,089,863
[45] Date of Patent: Jul. 18, 2000

[54] FLEXIBLE MOLD AND DENTAL MODEL FORMED THEREFROM

[76] Inventor: Edwin T. Van Valey, 95 Concord Rd., Sudbury, Mass. 01776

[21] Appl. No.: 09/236,155

[22] Filed: Jan. 22, 1999

Related U.S. Application Data

[63] Continuation-in-part of application No. 08/916,533, Aug. 21, 1997, Pat. No. 5,957,688.
[60] Provisional application No. 60/024,297, Aug. 22, 1996.

[51] Int. Cl.⁷ ...................................................... A61C 19/00
[52] U.S. Cl. ................................................. 433/34; 433/60
[58] Field of Search ................................ 433/34, 60, 64, 433/65, 213

[56] References Cited

U.S. PATENT DOCUMENTS

| | | | |
|---|---|---|---|
| 1,743 | 8/1840 | Evens . | |
| 400,713 | 4/1889 | Slack et al. . | |
| 750,203 | 1/1904 | Knight . | |
| 1,045,586 | 11/1912 | Montague . | |
| 1,338,918 | 5/1920 | Hall | 433/63 |
| 2,138,254 | 11/1938 | Mink | 18/5.7 |
| 2,430,177 | 11/1947 | Johnson et al. | 32/32 |
| 3,092,909 | 6/1963 | Miller | 32/32 |
| 3,097,431 | 7/1963 | Harris | 32/32 |
| 3,281,901 | 11/1966 | Davis et al. | 18/34.1 |
| 3,466,750 | 9/1969 | Timberlake et al. | 32/32 |
| 3,727,311 | 4/1973 | Schoonebeek | 32/32 |
| 3,966,165 | 6/1976 | Psensky | 249/120 |
| 3,998,422 | 12/1976 | Putzer | 249/117 |
| 4,096,632 | 6/1978 | Perry | 32/32 |
| 4,122,606 | 10/1978 | Roman | 32/11 |
| 4,182,507 | 1/1980 | Bekey et al. | 249/54 |
| 4,200,981 | 5/1980 | Fine | 433/60 |
| 4,207,677 | 6/1980 | Lampert | 433/60 |
| 4,251,209 | 2/1981 | Bekey et al. | 433/34 |
| 4,252,523 | 2/1981 | Gayso | 433/60 |
| 4,265,619 | 5/1981 | Lucki et al. | 433/54 |
| 4,299,570 | 11/1981 | Yogosawa | 433/62 |
| 4,365,783 | 12/1982 | Kesling | 249/124 |
| 4,382,787 | 5/1983 | Huffman | 433/64 |
| 4,412,822 | 11/1983 | Blechner | 433/60 |
| 4,449,930 | 5/1984 | Huffman | 433/64 |
| 4,451,234 | 5/1984 | Oye | 433/54 |
| 4,481,162 | 11/1984 | Huffman | 264/334 |
| 4,533,323 | 8/1985 | Huffman | 433/60 |
| 4,548,581 | 10/1985 | Huffman | 433/64 |
| 4,734,033 | 3/1988 | Huffman | 433/60 |
| 4,786,253 | 11/1988 | Morais | 433/60 |
| 4,842,242 | 6/1989 | Huffman | 249/54 |
| 4,865,544 | 9/1989 | Scruggs | 433/64 |
| 5,026,279 | 6/1991 | Wilkes | 433/60 |
| 5,046,949 | 9/1991 | Richardson | 433/57 |
| 5,076,786 | 12/1991 | Callne | 433/60 |
| 5,141,433 | 8/1992 | Peterson | 433/64 |
| 5,221,203 | 6/1993 | Callne | 433/58 |
| 5,360,337 | 11/1994 | Westdyk | 433/64 |
| 5,425,636 | 6/1995 | Ghim | 433/64 |
| 5,622,497 | 4/1997 | Cho | 433/60 |
| 5,769,634 | 6/1998 | Choi | 433/64 |

FOREIGN PATENT DOCUMENTS

| | | |
|---|---|---|
| 572850 | 11/1958 | Belgium . |
| 1 193 122 | 9/1985 | Canada . |
| 1124255 | 10/1956 | France . |
| 446682 | 6/1927 | Germany . |
| 596232 | 12/1947 | United Kingdom . |
| 2098070A | 11/1982 | United Kingdom . |

*Primary Examiner*—John J. Wilson
*Attorney, Agent, or Firm*—Hamilton, Brook, Smith & Reynolds, P.C.

[57] ABSTRACT

A flexible mold for forming the base of a dental model includes a cylindrical element which defines a mating element of a pivot mechanism that provides angular adjustment and subsequent fixation of a corresponding connection element of a dental model articulator.

8 Claims, 13 Drawing Sheets

FLEXIBLE MOLD AND DENTAL MODEL FORMED THEREFROM

RELATED APPLICATIONS

This application is a continuation-in-part of application Ser. No. 08/916,533 filed Aug. 21, 1997, now U.S. Pat. No. 5,957,688 which claims to benefit of U.S. Provisional application Ser. No. 60/024,297 filed Aug. 22, 1996. The entire teachings of the above-referenced applications are incorporated herein by reference.

BACKGROUND OF THE INVENTION

In the fabrication of dental prosthetics, such as false teeth or caps, a negative impression is made of the teeth of a dental patient using a thermoplastic material. The negative impression is then filled with a hardenable material to form a die. The die is affixed to a base formed of similar hardenable material to form a dental model. A dental model articulator is used to correlate upper and lower dental models in the forming and adjustment of the dental prosthesis.

The appeal of using a one-use or dispensable articulator is one primarily of time. A reusable articulator needs to be mounted to the models of the teeth with dental plaster, which requires considerable time in the processes of mixing, placing, curing, clean-up and then the subsequent removal of the hardened plaster from the models and articulator after completion of the prosthesis so as to allow re-use of the articulator. Dispensable articulators can save the time involved with these steps and have the added advantages of allowing the completed work to be returned to the dentist still articulated to allow verification of the mounting and to increase the presentation value of the case. Typically, a one-use articulator is secured to the dental models using an adhesive, thereby eliminating the use of plaster. To allow this, the articulator must provide a mechanism to adapt glueable members to angular differences of surfaces on the models. Such a mechanism is not needed as part of a reusable articulator because its members are allowed a large range of angular and positional differences within the masses of plaster that are used to affix the articulator to the models.

Multiaxial adaptation is a primary consideration in designing a successful one-use articulator. One approach is to use an adaptive pivot mechanism that allows multiaxial adjustment between a hinge and one or both models. U.S. Pat. Nos. 4,382,787, 4,865,544 and 5,425,636 disclose articulator designs that adapt to the models using ball and socket joints which are then immobilized with adhesive or friction. This approach forces a tradeoff, in that the joints must be kept small in order to provide the required amount of angular adjustment which in turn reduces the surface area of the joints, thereby limiting reliable immobilization.

Another approach of adaptation is to use an extensible member or members and allow adjustment of these in conjunction with a hinge joint axis to provide accommodation of these glueable surfaces to the differences of the orthogonal axes that share each of the top and bottom surfaces of the models. Accommodation of the remaining axes of difference orthogonal to these surfaces is accommodated simply by allowing a range of angular adjustment about these axes when gluing to these surfaces. Examples of this type are found in U.S. Pat. Nos. 5,046,949 and 5,221,203. A drawback to this approach is that the articulators are typically more complex in design and are larger in size and material requirements, as they have to provide structure both above and below the models which makes this type more expensive to produce than the previous examples which can be affixed to the posterior surfaces of the models. A primary shortcoming found in all of these and all prior art one-use articulators observed and researched is the inability to properly allow for lateral and protrusive translatory motions between the articulated models.

An early dental related patent, U.S. Pat. No. 1743, dated Aug. 28, 1840, describes a dental articulator that has provision for "action similar to that of the living subject" which is accomplished by using a sliding point of axis in the articulating joints to allow for these "live" translatory motions. Since then, many types and forms of dental articulators have been patented and manufactured ranging from extremely complex and expensive devices, to the more recent trend of using disposable or dispensable one-use articulators. U.S. Pat. No. 3,727,311 describes a very simple design connecting the models with a single resilient rod. This resilience allows translational motions, but this design lacks true hinging action. The previously mentioned U.S. Pat. No. 5,046,949 has a conventional hinge, but has no inherent provision for allowing translatory motions.

An articulator in wide use today is disclosed in U.S. Pat. No. 4,449,930, which is a continuation-in-part to the previously mentioned 4,382,787, and U.S. Pat. No. 4,548,581 which discloses the same articulator. The articulators disclosed in the '930 and '581 patents attempt to allow functional translatory motions by having the technician flex bracket members connecting the models to the hinge. However, this flexing requires considerable force which inhibits the feel of the natural motion paths. Also, the forces of this flexing exacerbate the aforementioned weakness of the adaptive ball and socket pivot mechanism. Because this one adaptive element allows motions on any axis before immobilization and has to withstand the flexing forces of both hinge arms after immobilization, the adhesive required to immobilize these motions is very critical, since it must lock all of the axial forces and also fix the socket half of the pivot mechanism to the model. This requires that the adhesive used in the joints be of high quality and that its application be technique sensitive. If misapplied or if the glue is old or too high in viscosity, then failure of the adhesive within the ball and socket joint or between the model and socket becomes likely.

In U.S. Pat. No. 4,449,930 the socket half of the adaptive joint is incorporated into the model base which simplifies the design. However, molding the socket into the base is not practical since it would eliminate the ability to laterally align the sockets to set the hinge axis sagittally perpendicular. To make this design approach practical, the socket needs to be a separate piece to allow it a range of lateral placement on the model which requires another glue joint to fix the socket to the model base. There is described in a related patent U.S. Pat. No. 4,481,162 a mold which forms a slot in the rear of the dental model for receiving a corresponding key on the socket half of the joint.

A further improvement on this same design by the same inventor is disclosed in U.S. Pat. No. 4,734,033. This improvement specifically addresses translatory motion by making the hinge brackets more flexible but even with this enhancement the articulator fails to allow true sliding motions between the models, since there is still strictly a single axis rotational motion allowed by the hinge joints.

Translational motions are an extremely important function to be provided by an articulator in the task of fabricating dental prosthetics. The technician must be able to freely check all of the possible lateral and protrusive motions that the patient uses in mastication. If the technician is impeded in doing this, then invariably the prosthesis will need adjustment by the dentist during placement in the mouth (or perhaps even remanufacture) which results in considerable aggravation for the patient and dentist. None of the prior art one-use articulators have been found to be both simple of design (to allow inexpensive manufacture and thus dispensability) and permissive of true translatory motions.

SUMMARY OF THE INVENTION

This invention relates to dental model articulators as used in the fabrication of dental prosthetics to provide and allow respective movements between an upper and lower set of dental models representing the natural dentition of the patient. More particularly, this invention relates to one-use articulators and to a flexible mold for forming the base of a dental model to have a connection element of a pivot mechanism for mating with such articulators.

An object of the present invention is to provide an articulator that does not inhibit the replication of true masticatory motions between articulated dental models.

Another object of the present invention is to provide an articulator that is very simple and hence inexpensive to produce.

Yet another object of the present invention is to provide an articulator that is not technique sensitive in its implementation.

Yet still another object of the present invention is to provide an articulator that requires a minimal amount of material to produce but still achieves a strong broad connection to the models.

Yet a further object of the present invention is to provide an articulator that does not require locking more than one axis of an adaptive pivot mechanism.

A still further object of the present invention is to provide a design that provides fewer and stronger adhesive connections to the models.

Another object of the present invention is to allow articulation of models with a large variation of dimensional differences.

Another object of the invention is to provide a mold to facilitate the forming of a dental model base to include a connection element of a pivot mechanism for mating with an articulator.

The present invention is directed to a dispensable articulator for the production of dental prosthetics that provides an accurate relative positioning of a corresponding pair of dental model casts. In the discussion of prior art one-use articulators it was pointed out that multiaxial adaptation is a key feature in the design of this type of articulator. The essence of the present invention is to combine this multiaxial motion into hinge joints and to provide pivot mechanisms connecting the articulator to the models that require only one axis of adjustment and subsequent fixation. Eliminating the need to lock or fuse multiaxial motions in adaptive pivot mechanisms is a primary advantage of the present invention.

Aside from the obvious and inherent strength of these adaptive joints needing only a single axis of adjustment, their lineal nature also allows the adjacent halves of these mechanisms for each model to be laterally combined, incorporated into and made to span the width of the model thus allowing a wide range of lateral positional placement for the mating elements without requiring the additional glue interfaces that would be manifest if these were separate components.

Accordingly, a preferred embodiment of a dental model articulator for connecting upper and lower dental models includes an arm having first and second arm segments and an intermediate hinge joint for joining the first and second arm segments to provide hinging motion about a hinge axis. The first and second segments each terminates at a distal end in an arm connection element that is pivotally engageable with a model connector of one of the upper and lower dental models. Each arm connection element is pivotable about a single pivot axis. The hinge joint comprises a node and a pair of cymbals having opposing undersurfaces which include detents for receiving the node therebetween. The node is attached to one of the first and second arm segments at a proximal end of the respective arm segment. The pair of cymbals is attached to the other of the first and second arm segments at a proximal end.

According to another aspect of the invention, a flexible mold forms a dental model base that includes cylindrical connection elements of a pivot mechanism for mating with corresponding connection elements of an articulator. A portion of the pivot mechanism is integrated into the dental model to simplify the design of the articulator. The pivot mechanism is lineal in nature thereby allowing adjacent halves of the articulator to be laterally combined and made to span the width of the model. This combination provides for a wide range of lateral positional placement for the mating connection elements of the articulator without requiring additional glue surfaces that could be needed for separate components.

Accordingly, a mold for forming a dental model base includes a bottom portion having a rear wall and a side wall at a periphery thereof which extends upwards to define a cavity. The walls have upper edges which define an opening to the cavity. The mold further includes a shaping element for forming a connection element of a pivot mechanism at the dental model base which rotationally mates with a corresponding connection element of the articulator.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
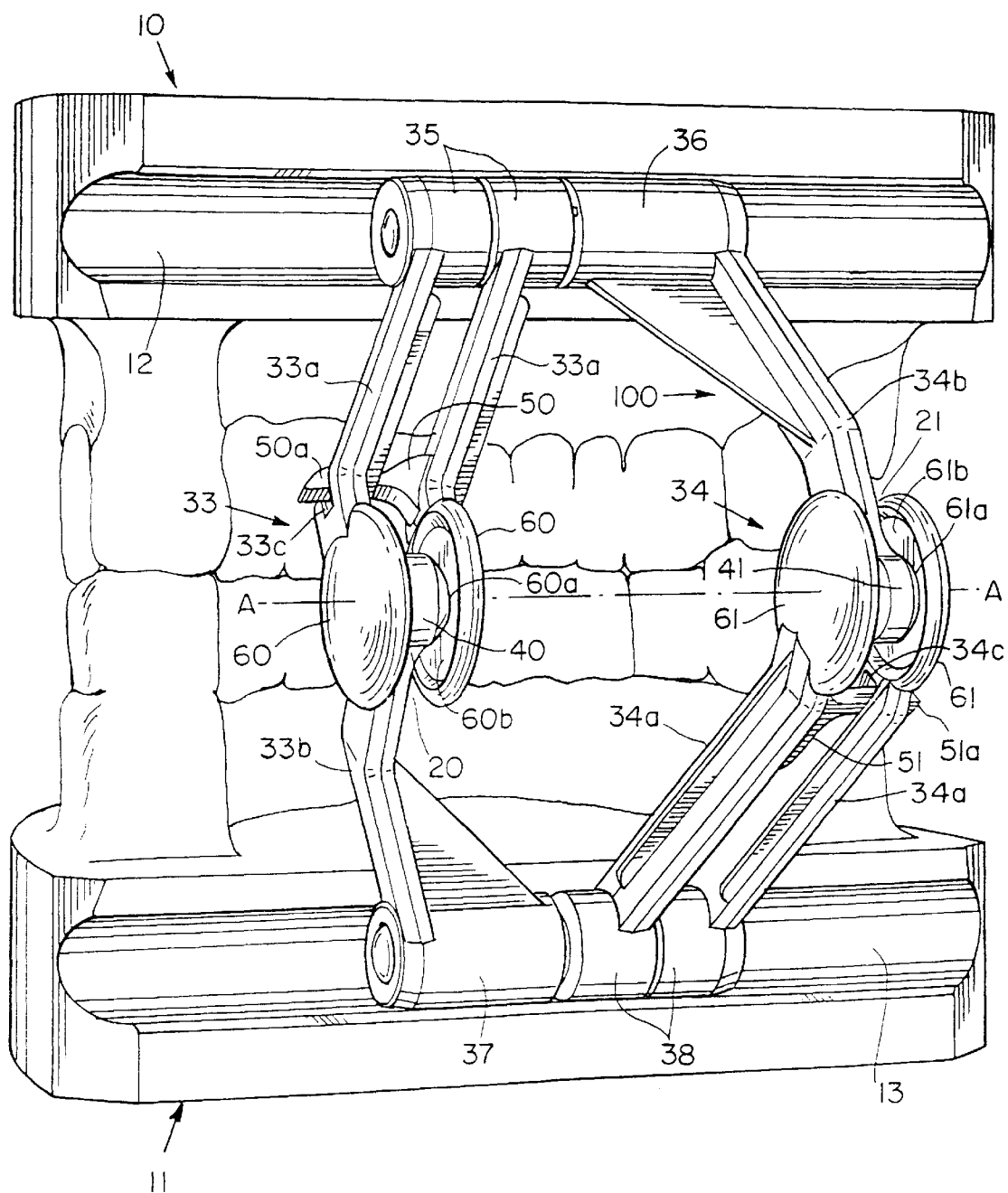
FIGS. 1 to 3 show perspective posterior, side and rear views, respectively, of a first embodiment of an articulator of the present invention having two articulator arms mounted to full arch dental models.

Referring to FIGS. 1–4, an embodiment of an articulator 100 redintigrating a pair of full arch dental models 10 and 11 is there shown. The articulator 100 comprises a pair of arms 33, 34 that are identical in structure. It should be noted that the following description generally employs a pair of reference characters to refer to a particular element or feature of the respective arms. The arms 33, 34 each include an arm segment 33b, 34b and a pair of parallel, bifurcated arm segments 33a, 34a. The parallel arm segments 33a, 34a terminate at a distal end in cylindrical rod-like elements 35, 38 and at a proximal end in a pair of coaxial cymbals 60, 61. The arm segment 33b, 34b terminates at a distal end in cylindrical rod-like element 36, 37 and at a proximal end in node 40, 41. The node is retained between the pair of cymbals 60, 61 supported by the bifurcated arm segments 33a, 34a to form a hinge joint 20, 21.

Figure 3:
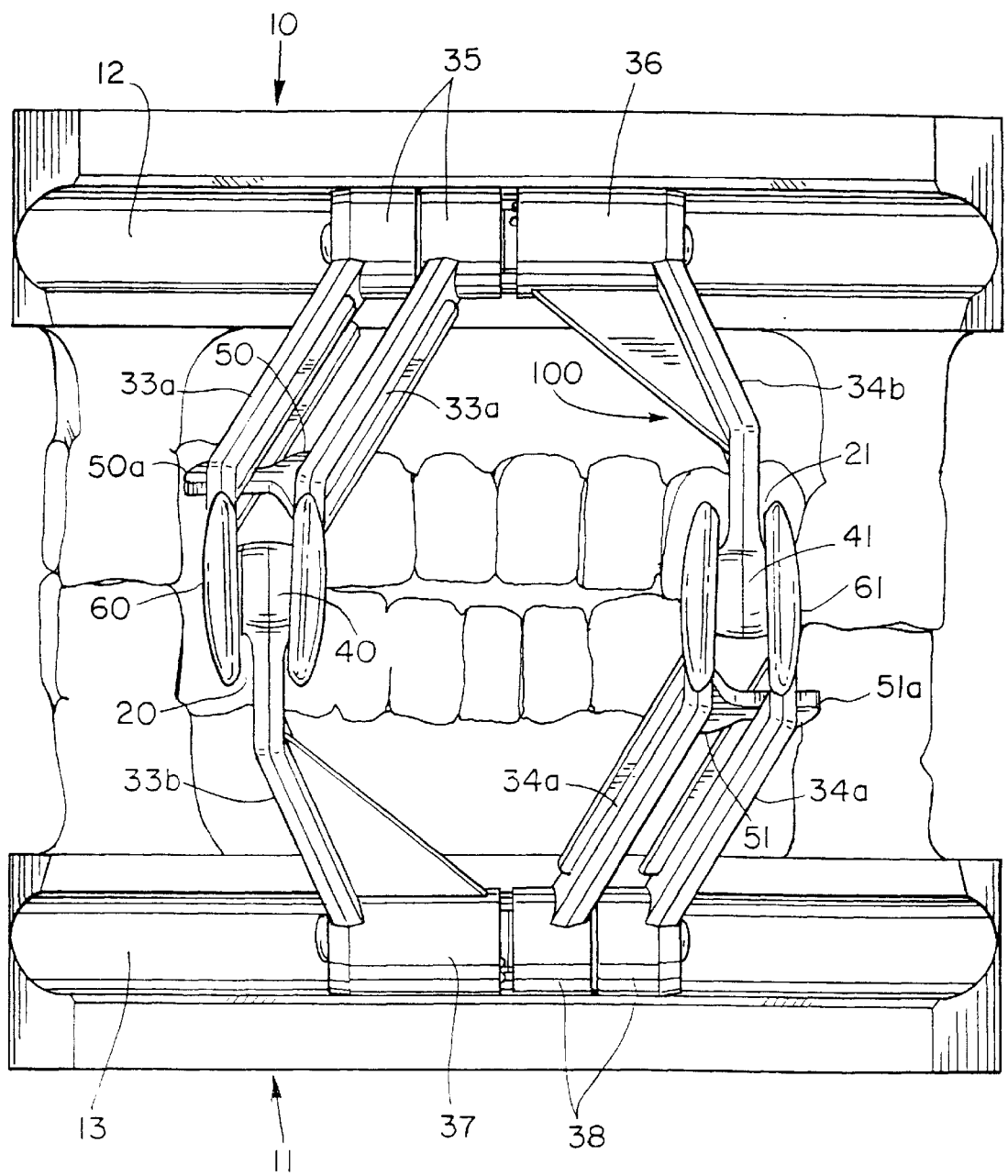
Figure 4:
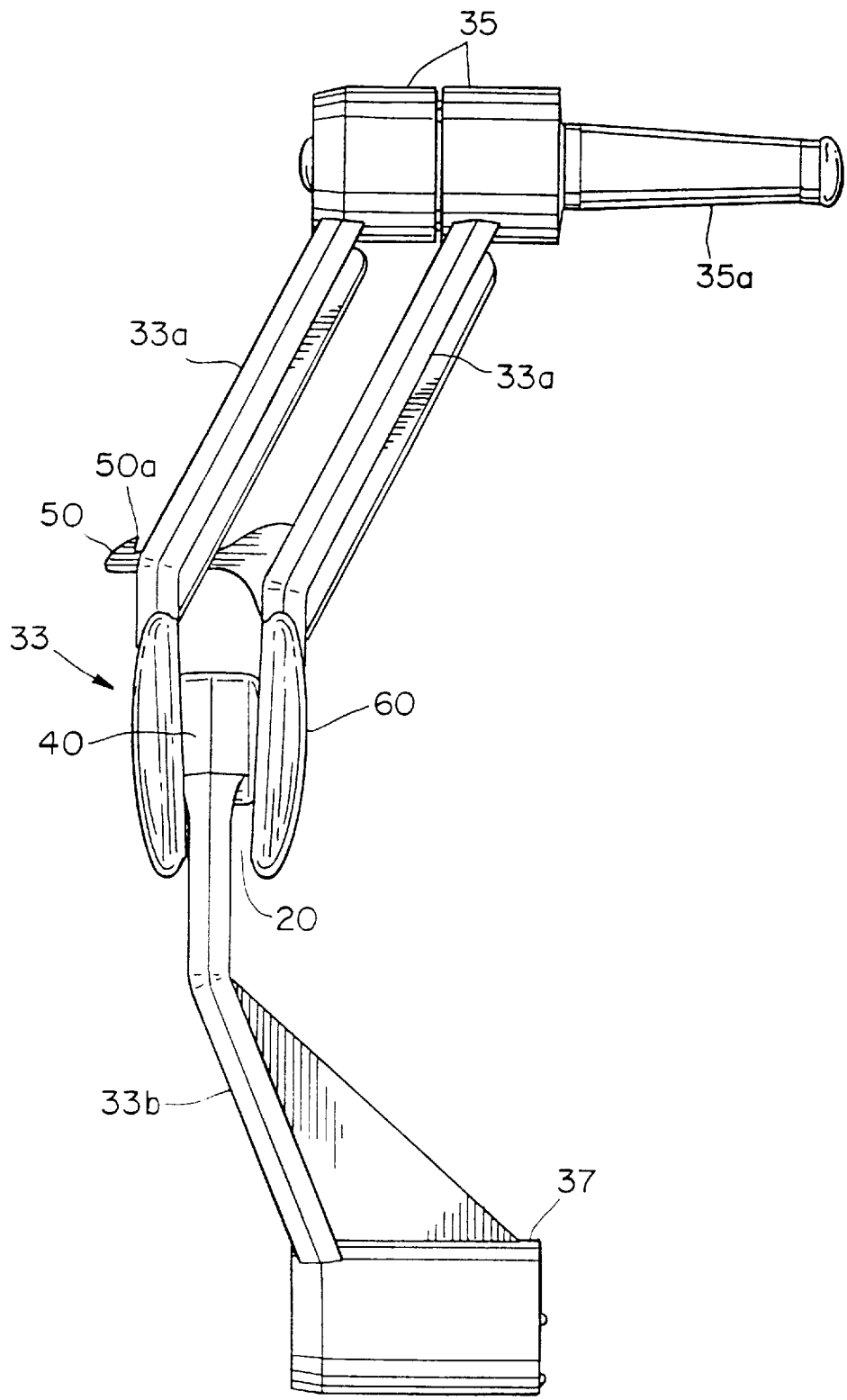
FIG. 4 is a rear view of one arm of the articulator of FIG. 1.
Figure 5:
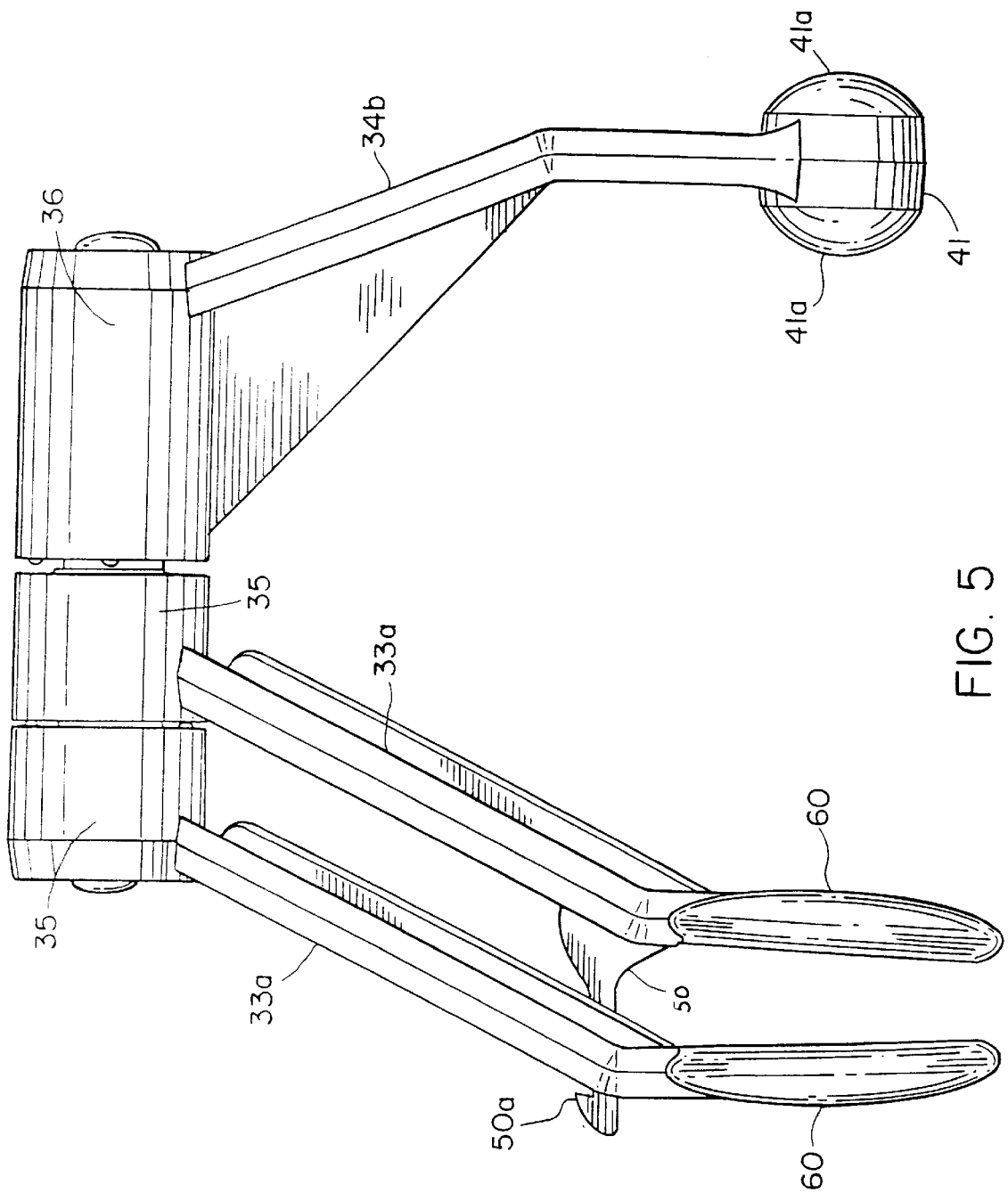
FIG. 5 is a rear view of either the upper or lower half of both arms of the articulator of FIG. 1 interconnected.

FIG. 4 illustrates arm 33 which is identical to arm 34. A preferred assembly of articulator 100 is formed by connecting the arms 33, 34 to each other in a complementary fashion to provide a single assembly for ease of handling. Specifically, the complementary connection is formed by snap-fitting cylindrical stem 35a into cylindrical rod-like element 36 and stem 38a into element 37 to form the articulator shown in FIGS. 1–3. Referring to FIG. 5, the portion of arm 33 that includes parallel arm segments 33a is shown connected to the portion of arm 34 that includes arm segment 34b.

A model connector defining a single axis pivot mechanism is incorporated into the base of each model 10, 11 in the form of transverse half-cylinders or channels 12 and 13 which traverse the posterior of the models (FIGS. 1 and 3). The channels can be either cut into the existing models or formed when the models are cast to provide connection at a range of angles about the radial axis of the transverse channels for mating the cylindrical rod-like elements 35, 36, 37, 38 which form the complement to these pivot mechanisms. While the channels 12, 13 are shown located on the posterior of the models, it is also possible to locate the channels at the top or bottom of the respective models. In alternate embodiments, the channels can instead be formed at the distal ends of the arm segments and the cylindrical elements can be incorporated in the models to provide the single axis connexus.

Figure 2:
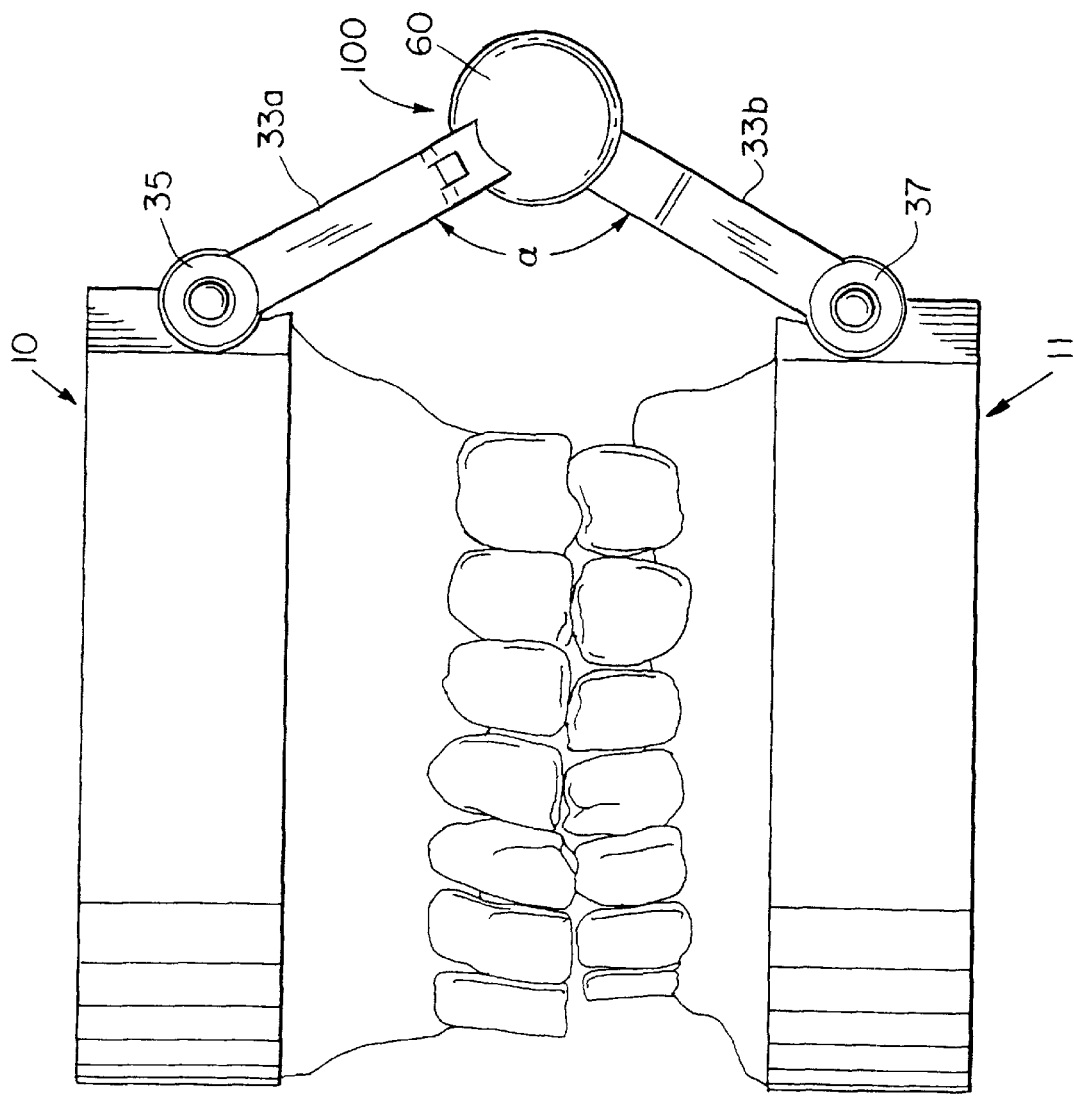

The cylindrical elements 35, 36, 37, 38 have sufficient transverse axial width such that any adjustment motion of the cylindrical elements within the channels is limited to radial motion about the channel axis and transverse motion along this axis. With the dental models placed at a closed and centric occlusal (i.e., closed bite) relationship as shown in FIG. 2, the arm segments of the respective arms intersect at an angle α of between approximately 40 to 170 degrees, the angle being dependent upon the vertical distance between the models 10 and 11.

It should be noted that while it is preferable to interconnect the arms 33, 34 to form a single assembly for ease of operation as described above, it is also possible to keep the arms 33, 34 unconnected for individual attachment to the dental models. This alternate configuration allows the arms 33, 34 to be separated laterally to provide a closer approximation to the positioning of the temporomandibular joints of the patient. The attachments of such unconnected arms can be made to the same channels 12, 13 or to separate channels on the models that need not be parallel nor coaxial.

Figure 6:
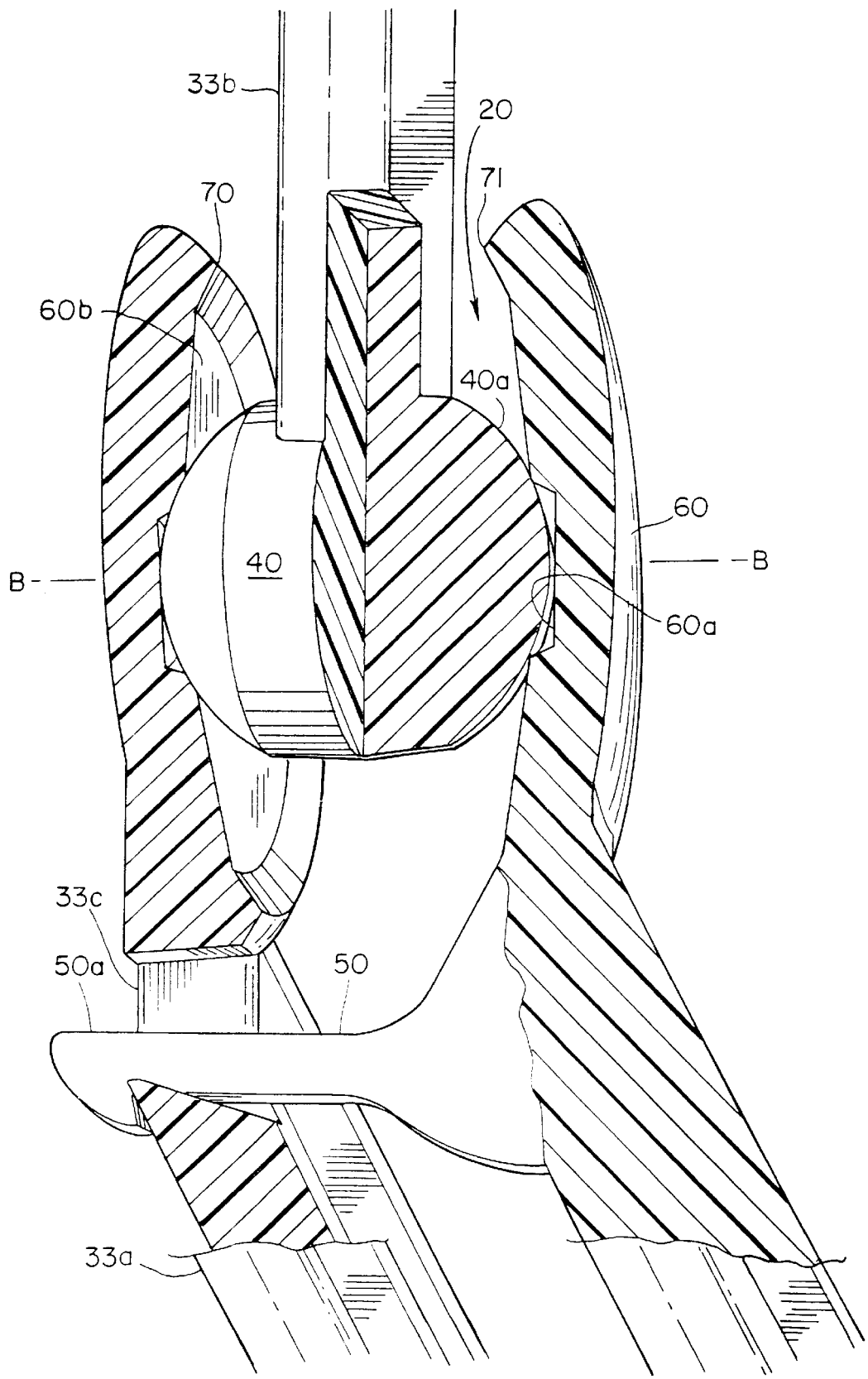
FIG. 6 is a partial cross-sectional view of one hinge joint of the articulator.

The multiaxial motion provided by the articulator of the present invention will now be described. Referring again to FIG. 5, node 40, 41 includes two opposed outwardly facing convex portions 40a, 41a. Referring to FIG. 6, a partial cross-section of one joint 20 of the articulator is shown. The cymbals 60, 61 are concave and toroidal in shape. When the node 40, 41 is engaged with the cymbals 60, 61, the convex portions 40a, 41a of each node 40, 41 are held in depressions or detents 60a, 61a at the center of each cymbal by resilience of the material in the bifurcated arm segment 33a, 34a.

The primary rotational motion of the node between the parallel arm segments is radial to an axis B that is shared coaxially by the cymbals. Because node 40, 41 and its connected arm segment 33b, 34b has no fixed axis when captured between the cymbals 60, 61, hinging motion between the arm segment 33b, 34b and parallel arm segments 33a, 34a is allowed an amount of orthogonal deviation from the axis B, that is, motion is provided about a set of orthogonal axes. This multiaxial motion of the hinge joint 20, 21 allows the cylindrical connection elements 35, 36, 37, 38 at the extremities of the arms 33, 34 to align with the nonparallelism that is likely to exist between the channels 12, 13 of models 10, 11.

Multiaxial motion is only required and exhibited during alignment of the articulator 100 to the models. Once the two arms of the articulator 100 are affixed to the models, the only axial motion allowed by the articulator between the models is about a single axis A defined together by the two hinge joints 20, 21 (FIG. 1). This common transverse hinge axis A lies interjacent and posterior to the dental models 10, 11 and is approximately perpendicular to a sagittal plane of the models.

Each bifurcated arm segment 33a, 34a includes a resilient pawl or latch 50, 51 that is used to increase or decrease pressure (i.e., compression) on the node 40, 41 between the cymbals 60, 61. The pawl includes a hooked portion 50a, 51a for engagement through opening 33c, 34c in the bifurcated arm segment 33a, 34a. When the pawl is engaged, it increases the resilient pressure on the node between the cymbals to an amount that effectively limits or restrains any motion between the arm segments 33a, 33b and 34a, 34b to rotational motion about the common axis A. Releasing the pawl lessens the resilience to an amount such that protrusive and retrusive motions are permitted between the articulated models 10, 11 by allowing the cymbals to move apart, thereby permitting the convexities of the node to slide across the surfaces 60b, 61b of the cymbals. This free sliding motion is then limited in excursion by ridges 70, 71 at the periphery of the cymbals. Note that while the multiaxial motion about the hinge joints 20, 21 is used for alignment of the articulator, the free sliding motion is used for simulation of lateral and protrusive translatory motions once the articulator has been aligned and mounted to the models.

Figure 7:
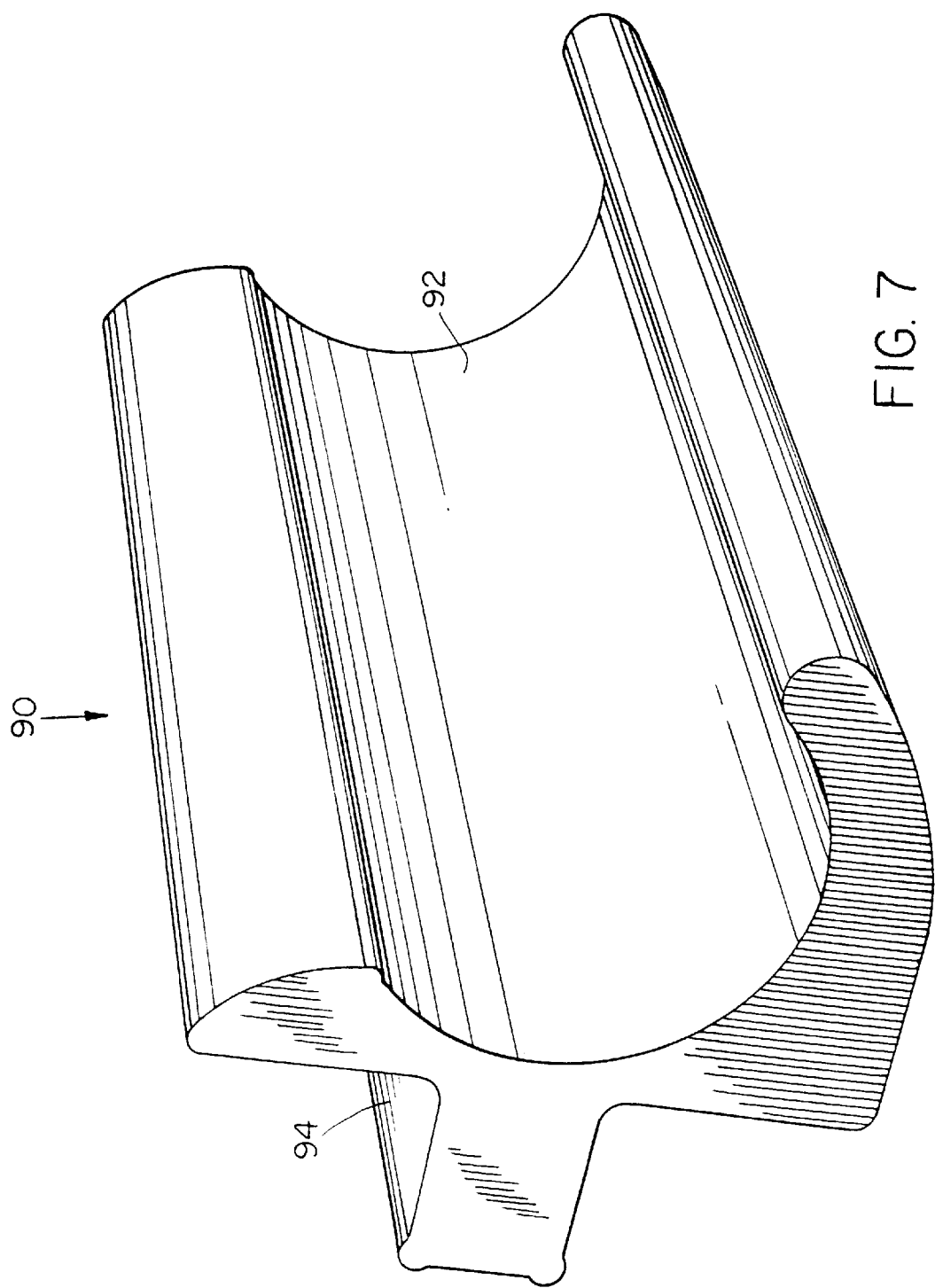
FIG. 7 is a perspective view of a clip for mounting to a dental model base in accordance with the present invention.

In an alternate embodiment, the channels can be in the form of clips that are affixed externally to the models. FIG. 7 shows a clip 90 that includes a channel 92 formed therein for receiving a cylindrical element of the arm segments. A transverse projection or shelf 94 extending along the length of the clip 90 is adapted for mounting the clip to a dental model base of the type having an indexing slot. Alternatively, a clip without the shelf 94 can be mounted directly to a flat wall of a dental model base.

Figure 8:
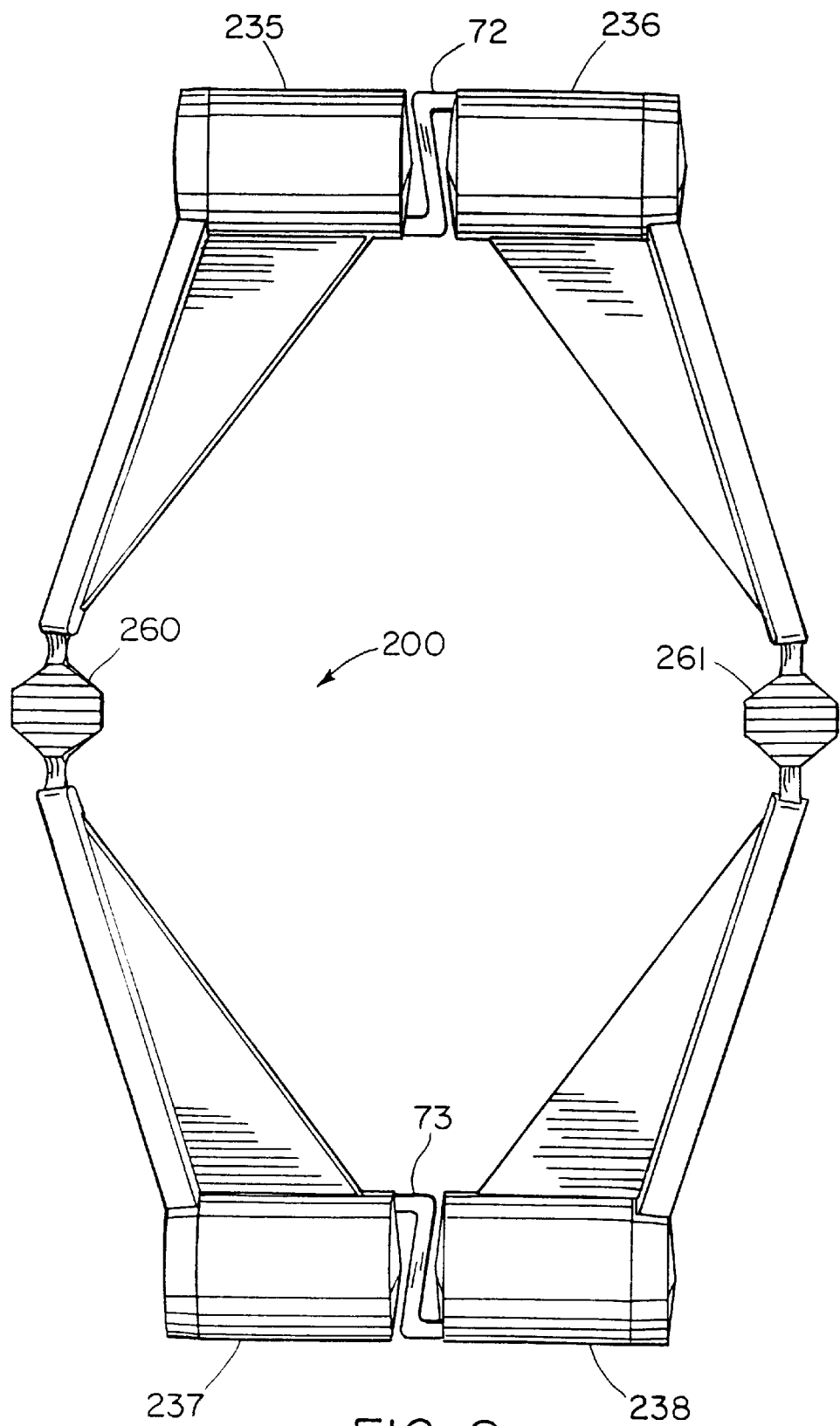
FIG. 8 is a rear view of an alternate embodiment of an articulator manufactured as a single piece.
Figure 9:
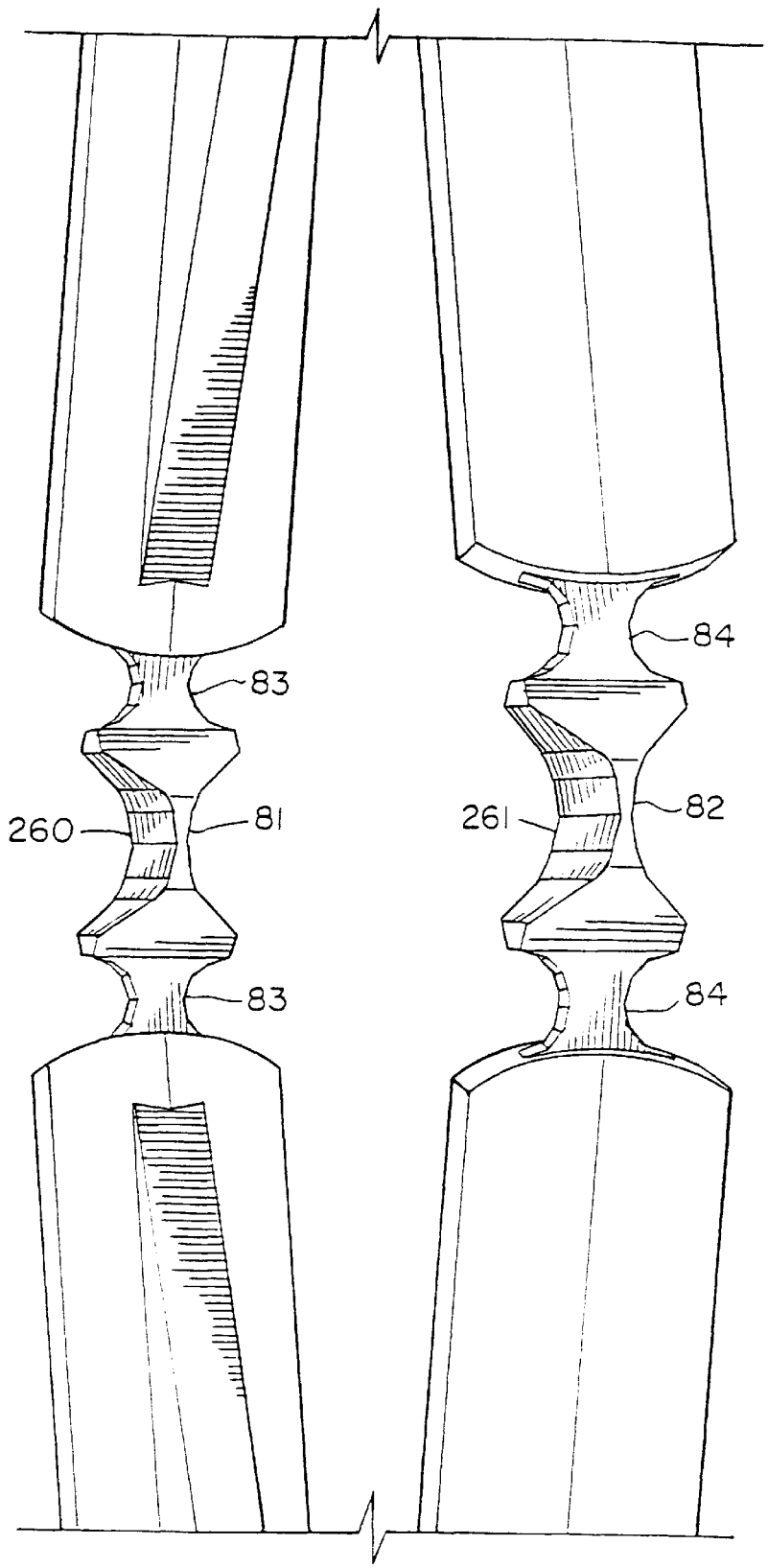
FIG. 9 is a perspective view of the hinge joints of the articulator of FIG. 8.

FIGS. 8 and 9 illustrate an alternate embodiment of an articulator 200 that provides simple hinging motion between the models and can be manufactured as one piece. In this embodiment, model connection elements 235, 236, 237, 238 are joined with webs 72 and 73 that allow separate torsional movements of the joined elements. Hinge elements 260, 261, which are best illustrated in FIG. 9, are relieved at areas 81 and 82 to promote the primary hinging action and are relieved at areas 83 and 84 to allow orthogonal alignment of the primary hinge axis. To use the articulator embodiments of the present invention, channels 12, 13 are cut or molded into the base of the dental models 10, 11. These channels 12, 13 are made with sufficient diameter and radial depth to receive the corresponding arm connection elements 35, 36, 37, 38 of the arms 33, 34. In alternate embodiments, the channels can be made to provide a slight interference frictional fit with the arm connection elements. In the case of the first embodiment, the mating segments 33a, 33b and 34a, 34b of each arm of articulator 100 (FIG. 1) are assembled so as to form two separate hinge jointed arms. The two arms 33, 34 are then joined together at their adjacent arm connection elements 35, 36, 37, 38 so that each pair of connection elements is held adjacent and coaxial. This allows the articulator 100 to be handled as one flexible unit as would be the case when handling the second embodiment 200 (FIG. 8) of the invention. The models 10, 11 are placed at the proper closed and centric occlusal relationship and held either by hand or other means known to a person skilled in the art of dental laboratory procedures. A temporary placement and alignment of the arm connection elements 35, 36, 37, 38 of the articulator 100 is made into the respective channels 12, 13 on the models by adjusting the angular relationships of the arms within the hinge joints 20, 21 defined by each node/cymbal pair 40, 60 and 41, 61 respectively. The articulator 100 is fixed by introducing an adhesive within the connexus formed between the arm connection elements 35, 36, 37, 38 and the model connection elements 12, 13 and allowing it to cure. Once fixed, the articulator hinge joints 20, 21 allow simulation of occlusal and masticatory motions between the models.

The articulator embodiments described herein are capable of being manufactured inexpensively. The articulators can be made of plastic such as nylon, glass-filled nylon, polycarbonate or glass-filled polycarbonate.

Figure 10:
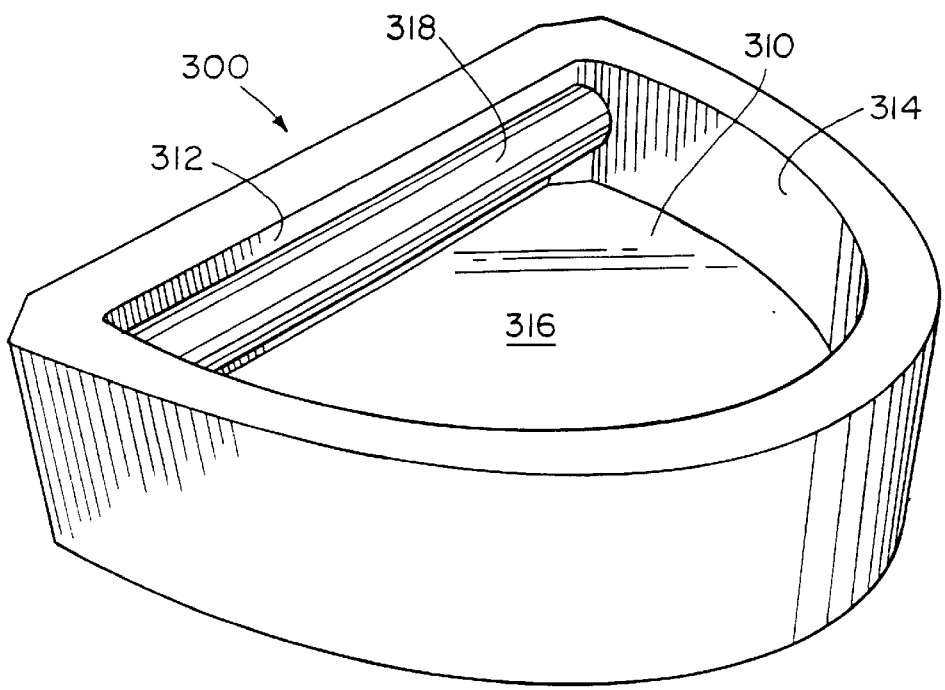
FIG. 10 is an illustration of a flexible rubber mold used to form a dental model base so as to include mating pivot mechanism elements for each arm of the articulator which are combined to form a single half-round channel traversing the posterior of the model.

Referring now to FIG. 10, a flexible rubber mold 300 suitable for forming a dental model base 400 (FIG. 11) for use with the articulator embodiments of the present invention is shown. A cross-sectional view of the mold 300 is shown in FIG. 12. The mold 300 is of flexible rubber construction and includes a cavity 310 formed by a back wall 312 and a curved side wall 314 projecting upward to edge 320 from a horizontal bottom portion 316. The back wall 312 includes a convex portion 318 that extends along the length of the back wall and into the cavity 310 for forming a half-round channel 410 traversing the posterior 412 of the dental model base 400. Preferably, the convex portion 318 extends horizontally along the full length of the back wall 312.

Figure 11:
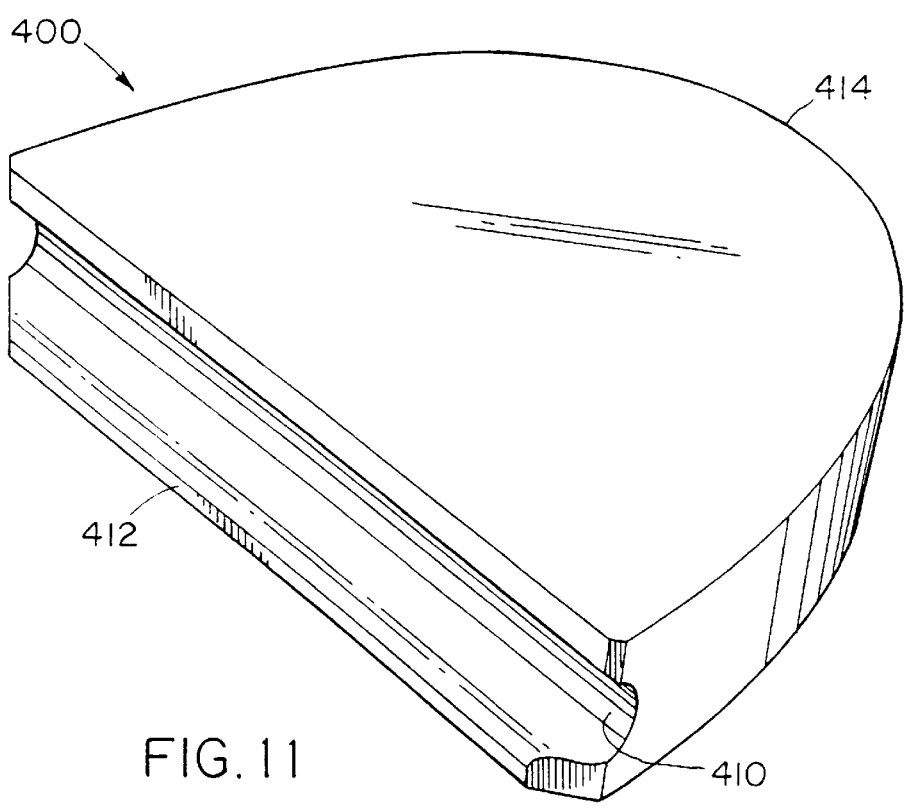
FIG. 11 is a dental model base such as would be formed by the mold of FIG. 10.
Figure 12:
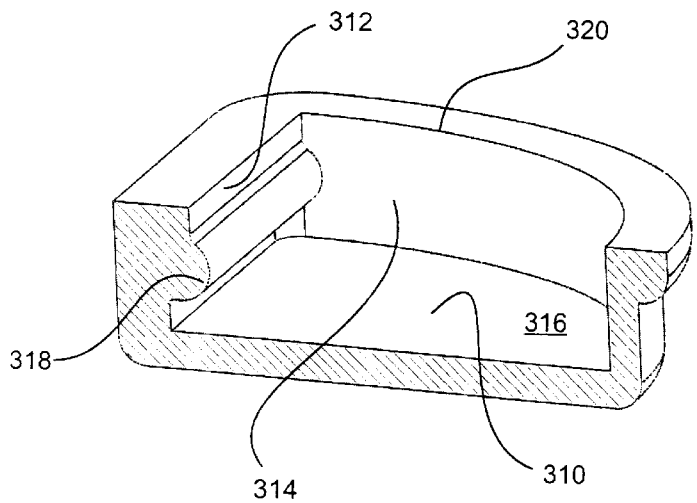
FIG. 12 is a cross-sectional view of the flexible rubber mold of FIG. 10.

To use the mold 300 to form the dental model base 400, which is shown in FIG. 11, a hardenable material such as pourable dental stone or plaster is poured into the mold. After the material hardens, the dental model base 400 is removed from the mold 300 by pushing upward against the bottom portion 316 to raise the anterior 414 of the dental model base upward about the convex portion 318 until the base completely disengages from the mold. The half-round channel 410 functions as a pivot mechanism element for receiving connection elements 35, 36, 37, 38 of articulator 100 or connection elements 235, 236, 237, 238 of articulator 200 as described hereinabove.

Figure 13:
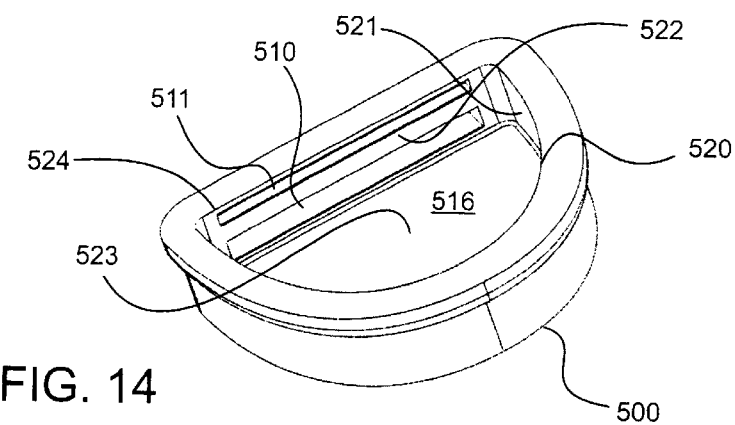
FIG. 13 is a perspective view of an alternate embodiment of a flexible mold used to form a dental model base.
Figure 14:
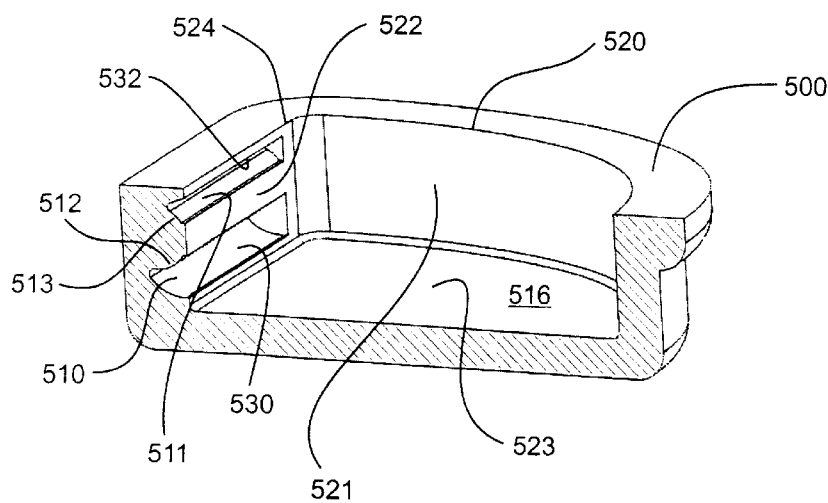
FIG. 14 is a cross-sectional view of the flexible mold of FIG. 13.

Referring now to FIGS. 13 and 14, an alternate embodiment of a flexible rubber mold 500 suitable for forming a dental model base 600 (FIG. 15) for use with the articulator embodiments of the present invention is shown. The mold 500 is of flexible rubber construction and includes a cavity 523 defined or formed by a back wall 522 and a curved side wall 521 projecting or extending upward from a horizontal bottom or floor portion 516. The upper edges 520, 524 of walls 522, 521 respectively define an opening to the mold.

The back wall 522 includes recesses 510, 511 which extend horizontally along a portion of the back wall. Recesses 510, 511 are spaced apart and are defined in part by excurvate cylindrical elements 512, 513, respectively, and by incurvate surfaces 530, 532, respectively, as shown in the cross-sectional view of FIG. 14. The excurvate cylindrical elements 512, 513 are longitudinal sections of a cylinder. The excurvatures of the excurvate cylindrical elements are coaxial with an axis lying between the recesses and oriented in a transverse relationship to the rear wall.

Figure 13A:
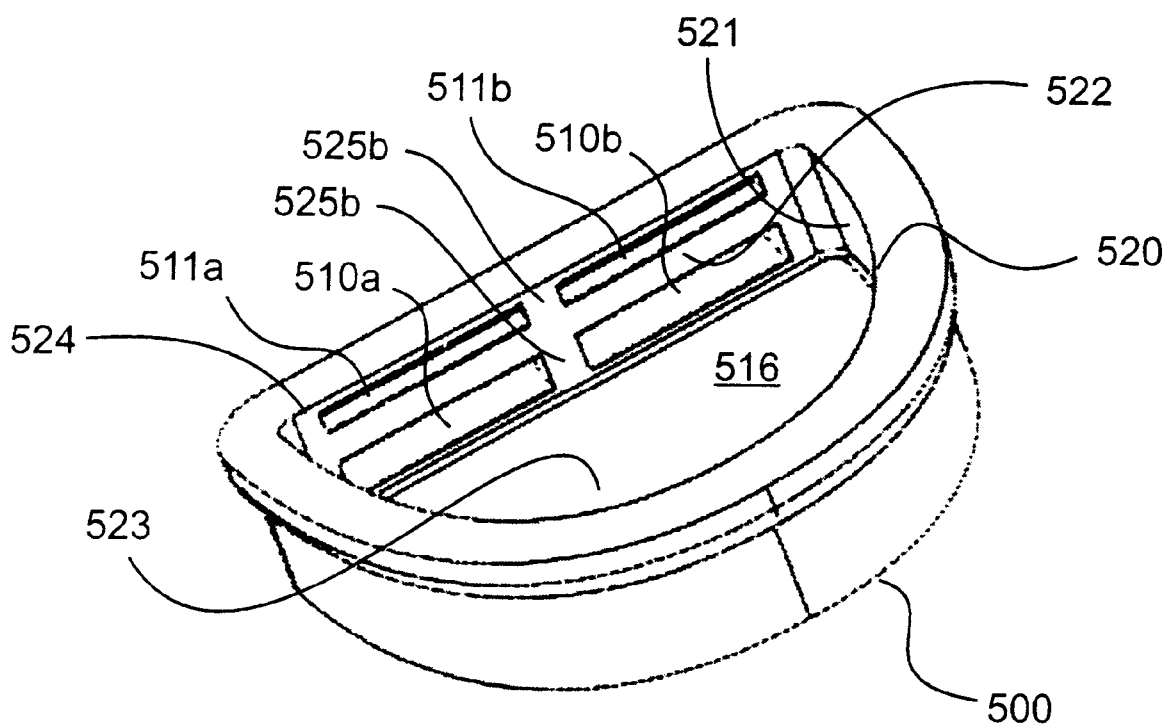
FIG. 13A is a perspective view of an alternate embodiment of a flexible mold having vertically separated recesses.

An alternate embodiment of the mold shown in FIG. 13A includes vertical portions 525a, 525b of the back wall 522 which separate recesses 510a, 510b and 511a, 511b. The vertical portions 525a, 525b form additional surfaces in the back wall of the base 600 described below.

Figure 15:
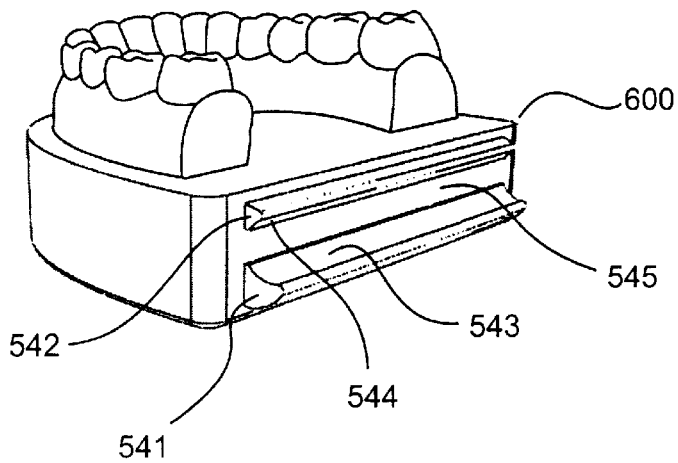
FIG. 15 is a perspective view of a dental model such as would be formed by the mold of FIG. 13 shown with a teeth model embedded therein.

The mold 500 can be used to form the dental model base 600 shown in FIG. 15 using pourable dental stone or plaster as described above. The dental model base 600 includes stanchions 541, 542 which protrude from a back wall 545 and correspond to recesses 510, 511, respectively. The stanchions 541, 542 include incurvate elements 543, 544 which correspond to and are formed by the excurvate elements 512, 513, respectively, of mold 500 (FIG. 14).

Figure 16:
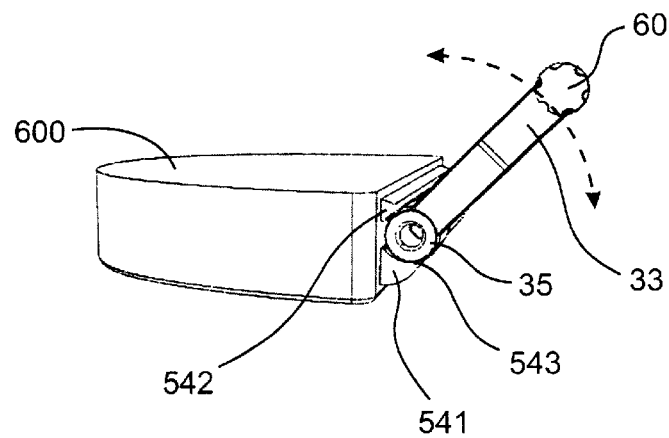
FIG. 16 is a perspective side view of the dental model of FIG. 15 shown engaged with an arm segment of the articulator of FIG. 1.

The incurvate elements 543, 544 function as a pivot mechanism element for receiving connection elements 35, 36, 37, 38 of articulator 100 or connection elements 235, 236, 237, 238 of articulator 200 as described hereinabove. This can be seen in FIG. 16, wherein an articulator arm 33 is shown connected to the stanchions 541, 542 of dental model base 600. In particular, connection element 35 of arm 33 engages with, or mates to, the incurvate elements 543, 544 to form a pivot mechanism at the dental model base with motion about a single pivot axis as shown.

Figure 17:
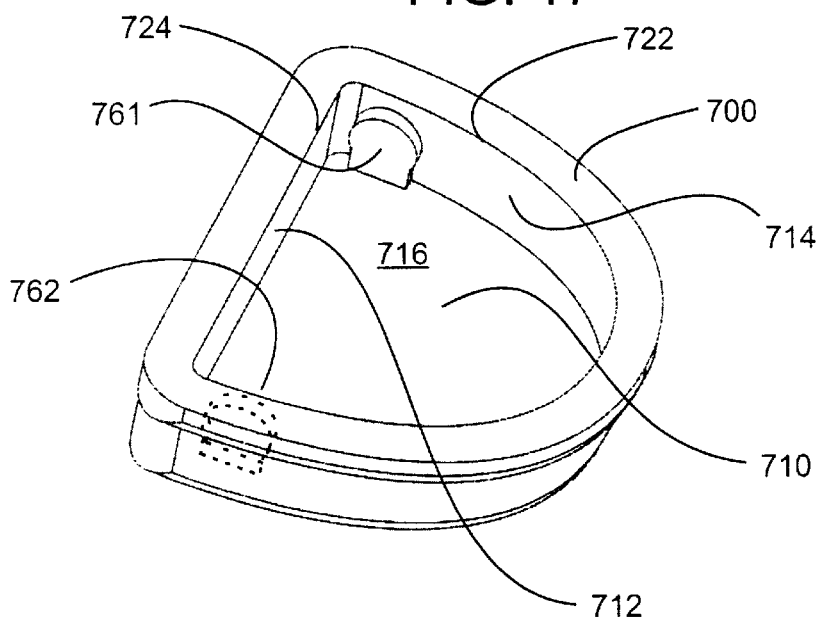
FIG. 17 is a perspective view of another alternate embodiment of a flexible mold used to form a dental model base.

Another alternate embodiment of a flexible mold 700 is shown in FIG. 17. The mold 700 includes a cavity 710 defined or formed by a back wall 712 and a curved side wall 714 projecting or extending upward from a horizontal bottom or floor portion 716. The upper edges 722, 724 of walls 712, 714 respectively define an opening to the mold. In this embodiment, the back wall 712 is essentially flat. The mold includes excurvate elements 761, 762 located at the sides of the mold cavity 710 and adjacent the back wall 712.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A mold for forming therein a dental model base useable with a dental articulator, the mold comprising:
    a bottom portion having a rear wall and a side wall at a periphery thereof extending upwards to define a cavity, the walls having upper edges defining an opening to the cavity; and
    a shaping element for forming a portion of the dental model base as a connection element of a pivot mechanism which rotationally mates with a corresponding connection element of the articulator wherein the rear wall includes a first recess and wherein the shaping element comprises a first excurvate cylindrical element in the first recess for forming at the dental model base a stanchion having an incurvature corresponding to the excurvature of the cylindrical element.

2. The mold of claim 1 wherein the rear wall further includes a second recess spaced apart from the first recess, the second recess including therein a second shaping element comprising a second excurvate cylindrical element, the excurvature of the first and second excurvate cylindrical elements are coaxial with an axis lying between the recesses and oriented in a transverse relationship to the rear wall.

3. A mold for forming therein a dental model base useable with a dental articulator, the mold comprising:
    a bottom portion having a rear wall and a side wall at a periphery thereof extending upwards to define a cavity, the walls having upper edges defining an opening to the cavity; and
    a shaping element for forming a portion of the dental model base as a connection element of a pivot mechanism which rotationally mates with a corresponding connection element of the articulator wherein the shaping element comprises a convex portion extending into the cavity for forming a concave channel at the dental model base to which channel the articulator can be attached to form a pivot mechanism.

4. The mold of claim 3 wherein the shaping element comprises a pair of convex portions formed at opposing ends of the side wall.

5. A mold for forming therein a dental model base useable with a dental articulator, the mold comprising:
    a bottom portion having a rear wall and a side wall at a periphery thereof extending upwards to define a cavity, the walls having upper edges defining an opening to the cavity; and
    a shaping element for forming a portion of the dental model base as a connection element of a pivot mechanism which rotationally mates with a corresponding connection element of the articulator wherein the shaping element comprises an excurvate cylindrical element for forming at the dental model base an incurvature corresponding to the excurvature of the cylindrical element.

6. The mold of claim 5 wherein the excurvature is on the rear wall and wherein a cylinder axis is oriented in a transverse relationship to the rear wall.

7. A method of forming a dental model base for use with a dental articulator, the method comprising the steps of:
    defining a mold cavity with a bottom portion having a rear wall and a side wall at a periphery thereof extending upwards;
    defining an opening to the mold cavity with upper edges of the walls;
    defining a shaping element for forming at the dental model base a connection element of a pivot mechanism which rotationally mates with a corresponding connection element of the articulator;
    pouring a hardenable material into the mold cavity to give specific form to said dental model base;
    removing the dental model base from the mold cavity upon hardening of the hardenable material by pushing upward against the bottom portion to raise the dental model base upward about the shaping element until the base disengages from the mold cavity.

8. A flexible mold for forming therein a dental model base useable with a dental articulator, the mold comprising:
    a horizontal bottom portion;
    a side wall projecting upward from the bottom portion and terminating in opposite ends;
    a back wall projecting upward from the bottom portion and terminating in opposite ends that join respective opposite ends of the side wall, the side wall and back wall together defining the perimeter of a mold cavity; and
    a transverse convex portion extending into the cavity for forming a concave channel within the dental model base to which channel the articulator can be attached to form a pivot mechanism.

* * * * *